US010222342B2

(12) United States Patent
Ortner et al.

(10) Patent No.: US 10,222,342 B2
(45) Date of Patent: Mar. 5, 2019

(54) METHOD AND DEVICE FOR DETECTING DEFECTS IN COILS OF BRITTLE OR FRACTURE-PRONE MATERIAL WHICH IS AT LEAST PARTIALLY TRANSPARENT, AND USE OF SAID METHOD AND DEVICE (71) Applicant: SCHOTT AG, Mainz (DE)

(72) Inventors: Andreas Ortner, Gau-Algesheim (DE); Fabian Wagner, Mainz (DE)

(73) Assignee: SCHOTT AG, Mainz (DE)

( * ) Notice: Subject to any disclaimer, the term of this patent is extended or adjusted under 35 U.S.C. 154(b) by 139 days.

(21) Appl. No.: 15/010,741

(22) Filed: Jan. 29, 2016

(65) Prior Publication Data
US 2016/0161423 A1 Jun. 9, 2016

Related U.S. Application Data (63) Continuation of application No. PCT/EP2014/064960, filed on Jul. 11, 2014.

(30) Foreign Application Priority Data

Aug. 1, 2013 (DE) .................. 10 2013 108 308

(51) Int. Cl.
G01N 21/958 (2006.01)
G01N 21/892 (2006.01)
(Continued)

(52) U.S. Cl.
CPC .......... *G01N 21/958* (2013.01); *G01B 11/30* (2013.01); *G01N 21/892* (2013.01);
(Continued)

(58) Field of Classification Search
CPC .... G01N 21/84; G01N 21/8422; G01N 21/86; G01N 21/88; G01N 21/89;
(Continued)

(56) References Cited

U.S. PATENT DOCUMENTS 2,386,511 A * 10/1945 Slayter .................... C03B 17/06
260/DIG. 41
2,910,805 A * 11/1959 Muller .................... C03B 17/06
65/176
(Continued)

FOREIGN PATENT DOCUMENTS

CH 397162 A * 8/1965 ............. C03B 17/06
DE 102011113670 A1 3/2013
(Continued)

OTHER PUBLICATIONS

English translation of Written Opinion of the International Searching Authority dated Oct. 13, 2014 for corresponding PCT/EP2014/064960, 7 pages.
(Continued)

*Primary Examiner* — Gordon J Stock, Jr.
(74) *Attorney, Agent, or Firm* — Ohlandt, Greeley, Ruggiero & Perle, L.L.P.

(57) ABSTRACT

A method and a device are provided for detecting defects in coils, such as rollable ultra-thin glass, rollable glass films, rollable laminated ultra-thin glasses or films, rollable solar cells, and rollable organic light emitting diodes (OLEDs). The method includes: providing a glass ribbon in a coil with a shape of a hollow cylinder with two end faces and one ribbon surface; introducing light into a first of the two end faces so that the light is directed from a light entrance side at the first of the two end faces to a light exit side at a second of the two end faces and exits from the light exit side; detecting the light at the light exit side with a first optical imaging detector so that, if a crack is present, the crack is seen as a shading in an image captured by the first optical imaging detector.

12 Claims, 4 Drawing Sheets (51) Int. Cl.
*G01N 21/90* (2006.01)
*G01B 11/30* (2006.01)
*G01N 21/896* (2006.01)
*G01N 21/89* (2006.01)

(52) U.S. Cl.
CPC ....... *G01N 21/8914* (2013.01); *G01N 21/896* (2013.01); *G01N 2201/061* (2013.01)

(58) Field of Classification Search
CPC ........... G01N 21/8901; G01N 21/8903; G01N 21/8914; G01N 21/8915; G01N 21/8916; G01N 21/892; G01N 21/8921; G01N 21/8922; G01N 21/894; G01N 21/896; G01N 21/898; G01N 21/8983; G01N 21/94; G01N 21/8803; G01N 21/9515; G01N 21/952; G01N 21/958; G01N 33/36; G01N 33/365; G01N 33/367; G01N 2201/061; G01N 2201/062; G01N 2201/0626; G01N 2201/0627; G01N 2201/063; G01N 2201/0638; G01N 2223/642; G01N 2223/643; G01N 2223/645; G01N 2223/646; G01N 2223/6462; G01N 2223/6466; G01N 2223/652; G01N 21/9803; G01N 2021/8427; G01N 2021/8438; G01N 2021/8444; G01N 2021/845; G01N 2021/8609; G01N 2021/8645; G01N 2021/869; G01N 2021/8841; G01N 2021/8845; G01N 2021/8854; G01N 2021/8858; G01N 2021/8861; G01N 2021/886; G01N 2021/8874; G01N 2021/888; G01N 2021/8887; G01N 2021/8902; G01N 2021/8904; G01N 2021/8905; G01N 2021/8907; G01N 2021/8908; G01N 2021/8924; G01N 2021/8925; G01N 2021/8927; G01N 2021/8928; G01N 2021/8962; G01N 2021/8967; G01B 11/30; G01B 11/303; G01B 11/306; G01B 11/8908; G01B 11/8924; G01B 11/8927; G01B 11/8928; G01B 11/8962; G01B 11/8967; G01M 11/088; G01M 11/30; G01M 11/33; G01M 11/335; G01M 11/35; G01M 11/37; G01M 11/39
USPC ......... 356/238.2–238.3, 239.1–239.3, 239.7, 356/239.8, 600, 429, 430, 431; 382/141, 382/152; 348/86, 88, 92
See application file for complete search history.

(56) References Cited

U.S. PATENT DOCUMENTS

| | | | | |
|---|---|---|---|---|
| 3,089,801 A * | 5/1963 | Tierney | ............. | B32B 17/10018 156/1 |
| 3,142,831 A * | 7/1964 | Horne | ................... | B65H 63/065 250/215 |
| 3,515,488 A * | 6/1970 | Houser | ............... | G01N 21/8916 250/208.4 |
| 4,258,846 A * | 3/1981 | Campo | ................... | B65H 18/28 206/412 |
| 4,303,436 A * | 12/1981 | Rossi | ...................... | C03B 17/06 65/170 |
| 4,928,904 A * | 5/1990 | Watts | .................. | B65H 54/2878 242/478.2 |
| 5,355,213 A | 10/1994 | Dotan | | |
| 5,723,857 A * | 3/1998 | Underwood | ......... | G01M 11/085 250/227.14 |
| 6,226,080 B1 | 5/2001 | Takeuchi et al. | | |
| 7,004,421 B2 * | 2/2006 | Hayashi | .................. | B29C 71/02 242/534 |
| 9,278,497 B2 * | 3/2016 | Mori | ......................... | B32B 3/02 |
| 9,581,521 B2 * | 2/2017 | Mejouev | .............. | G01M 11/088 |
| 9,676,579 B2 * | 6/2017 | Mori | .................... | B65H 23/195 |
| 2005/0018199 A1 * | 1/2005 | LeBlanc | .............. | G01N 21/958 356/477 |
| 2005/0184259 A1 | 8/2005 | Terui | | |
| 2011/0014445 A1 * | 1/2011 | Hawtof | ................... | C03B 19/14 428/220 |
| 2011/0023548 A1 * | 2/2011 | Garner | ..................... | B32B 17/06 65/106 |
| 2011/0177325 A1 * | 7/2011 | Tomamoto | ............. | B65H 18/28 428/332 |
| 2011/0192878 A1 * | 8/2011 | Teranishi | ................. | C03B 17/06 226/1 |
| 2011/0200812 A1 * | 8/2011 | Tomamoto | ............. | B65H 18/28 428/220 |
| 2012/0017642 A1 * | 1/2012 | Teranishi | ............. | B28D 5/0011 65/105 |
| 2012/0047951 A1 * | 3/2012 | Dannoux | ................ | C03B 17/06 65/25.3 |
| 2012/0131955 A1 * | 5/2012 | Kuroiwa | ............... | C03B 23/037 65/24 |
| 2012/0131962 A1 * | 5/2012 | Mitsugi | ............... | C03B 33/0235 65/112 |
| 2016/0137543 A1 * | 5/2016 | Abramov | ............ | C03B 33/0215 225/2 |

FOREIGN PATENT DOCUMENTS

| | | | | |
|---|---|---|---|---|
| EP | 2312382 A1 | 4/2011 | | |
| JP | H08152416 A | 6/1996 | | |
| JP | H08261953 | 10/1996 | | |
| JP | H09133638 | 5/1997 | | |
| JP | 2007119322 A * | 5/2007 | | |
| JP | 2010194874 A * | 9/2010 | | |
| JP | 2010223792 | 10/2010 | | |
| JP | 2011075296 | 4/2011 | | |
| JP | WO 2011102271 A1 * | 8/2011 | .......... | C03C 17/007 |
| JP | 2013079181 A * | 5/2013 | | |
| WO | 2013181060 | 12/2013 | | |
| WO | WO 2014085449 A1 * | 6/2014 | .......... | C03B 33/0215 |

OTHER PUBLICATIONS

English translation of the International Preliminary Report on Patentability dated Feb. 2, 2016 for corresponding PCT/EP2014/064960, 8 pages.
English translation of International Search Report dated Oct. 13, 2014 for corresponding PCT/EP2014/064960, 2 pages.

* cited by examiner

METHOD AND DEVICE FOR DETECTING DEFECTS IN COILS OF BRITTLE OR FRACTURE-PRONE MATERIAL WHICH IS AT LEAST PARTIALLY TRANSPARENT, AND USE OF SAID METHOD AND DEVICE

CROSS REFERENCE TO RELATED APPLICATIONS

This application is a continuation of International Application No. PCT/EP2014/064960 filed on Jul. 11, 2014, which claims the benefit under 35 U.S.C. § 119(a) of German Patent Application No. 10 2013 108 308.0 filed on Aug. 1, 2013, the entire contents of each of which are incorporated by reference herein.

BACKGROUND

1. Field of the Invention

The invention generally relates to the detection of defects or faults, such as bubbles, inclusions, cracks, etc., in ribbons of brittle or fracture-prone material which is at least partially transparent, when the ribbon is being or has been wound into a coil. More particularly, the invention relates to the localization and classification of defects such as cracks in rolled glass ribbons or glass coils.

2. Description of Related Art

In the manufacturing of ultra-thin glasses, i.e. glasses having a thickness of less than or equal to 200 µm, the highly flexible glass ribbon is subjected to strong vibrations, due to the high speed of the moving glass ribbon and the drawing of the so-called glass films at a high drawing rate, such vibrations being of an extent so as to go beyond the small focus range of high resolution optics. A result therefore is increased slip and increased misclassification of detected defects. Furthermore, it is observed that when a ribbon that has been detected as error-free glass is wound into a coil, the ribbon in the coil may break as a result of stresses in the edge region caused by the bending operation or due to an increase in the surface load on the coil. If an edge previously has been damaged with microcracks, smallest tensile stresses may cause breakage of the glass. Microcracks may for instance be caused either inherently by the molding, cooling, and transfer processes, or by the cutting of the border, i.e. the edge region of the glass ribbon.

The detection of cracks in the glass ribbon coil is crucial for transport and further processing of the glass ribbon, for example for outgoing inspection at the producer, or for incoming inspection at the customer. As part of quality inspection it is for example important to determine how many cracks exist in the coil and at which positions and what is the length of the defect-free glass ribbon between the cracks. With the knowledge of crack positions, it can be prevented that previously damaged glass or glass residues or glass splinters are introduced into the systems for further processing.

SUMMARY

Therefore, the invention is based on the object to enable and improve the detection of defects, both inline and offline, in ribbons of brittle or fracture-prone material which is at least partially transparent and which ribbon is being wound or has been wound into a coil.

Furthermore, it should be possible to continuously monitor the winding process, that is the rolling and unrolling, or winding and unwinding of the coil, for occurrence of defects, in particular cracks, and preferably to classify the coiled ribbon material in terms of its freedom from defects, at least per layer or section of the ribbon.

Accordingly, the invention provides a method for detecting or inspecting defects, in particular cracks, in ribbons of brittle or fracture-prone material which is at least partially transparent, wherein the ribbon is wound into a coil, the ribbon having ribbon surfaces and edge surfaces, wherein the wound ribbon forms a coil with a shape of a hollow cylinder in which the coiled edge surfaces define the two end faces and one of the ribbon surfaces defines the outer circumferential surface of the hollow cylinder; wherein light is introduced into an end face of the coil while either the coil is stationary or the coil rotates and the ribbon continues to be wound up or unwound; wherein in the coil the light is directed from the light entrance side end face to the light exit side end face of the coil and exits from the light exit side end face; wherein the light exiting from the end face of the coil is detected by means of an optical imaging detector. A defect, in particular a crack, therefore becomes apparent as a shading in the image captured by the optical imaging detector as a result of interruption of light transmission due to the defect.

Therefore, the longitudinal position of the defect can be determined from the position of the shading on the image, for example automatically, by an image processing means. According to one embodiment of the invention, in order to be able to also determine the position of a defect transversely to the longitudinal direction of the ribbon, or in order to get further information about the nature of the defect, a second optical imaging detector which faces the outer circumferential surface may be provided. In case of a defect, in particular a crack, the second optical imaging detector (D2) facing the outer circumferential surface can thus detect the light deflected in the coil by being scattered at the defect, in particular crack, so as to exit from the outer circumferential surface. The scattering position in the direction transversely to the longitudinal direction in the captured image then gives the transverse position of the defect.

Light, herein, basically and preferably refers to ambient light and/or additionally injected light which is emitted by a dedicated light source of the device according to the invention. In addition to visible light, the term light also includes infrared light or infrared radiation, for example when employed for detection in rollable solar cells. Optionally, UV-light may be used as well.

Accordingly, a device for detecting defects, in particular cracks, in ribbons of brittle or fracture-prone material that is at least partially transparent, which is adapted for carrying out the method described above, comprises: means for winding or unwinding the ribbon into or from a coil with the shape of a hollow cylinder in which the coiled edge surfaces define the two end faces and one of the ribbon surfaces defines the outer circumferential surface of the hollow cylinder; a light source which is arranged with respect to the means for winding or unwinding the ribbon such that the light is introduced into an end face of the coil, while either the coil is stationary or the coil rotates and the ribbon continues to be wound or unwound, wherein in the coil the light is directed from the light entrance side end face to the light exit side end face of the coil and exits from the light exit side end face; an optical imaging detector (D1) detecting the light exiting from the end face of the coil (bright-field arrangement), so that a defect, in particular a crack, can be seen as a shading in the image captured by the optical imaging detector (D1) caused by interruption of light transmission due to the defect.

According to one embodiment of the device according to the invention, a second optical imaging detector (D2) is provided which faces the outer circumferential surface and which in case of a defect, in particular a crack, in the ribbon detects the light deflected in the coil by being scattered at the defect, in particular crack, so as to exit from the outer circumferential surface (dark-field arrangement).

Defects in the ribbon will thus cause a deflection of the directed light out of the monitoring direction of the first detector (D1), preferably a photodiode or a camera, and will therefore cause a local variation in intensity of the light beams at the one or more detectors, D1 and D2. Generally, this results in a reduction of the intensity of the light beams in the defect projection area at the first detector (D1) and in an increase of the intensity of the light beams at the second detector (D2), preferably a second camera.

The advantage of inspection or detection in the coil is that in the rolled-up or wound-up state the ribbon is in a mechanically defined position and therefore almost free of vibrations. This is in particular the case when the coil is wound to or unwound from a drum mounted on an axle. Accordingly, it is possible to simultaneously inject light into a plurality of or into all layers of the coiled ribbon, so that in this manner different layer areas of the coil can be inspected or detected simultaneously. Generally, during winding or unwinding, individual layers of the wound ribbon will in particular be inspected repeatedly.

The scattered light scattered at a defect or crack may pass through overlying layers of the coil and exit from the outer circumferential surface of the hollow cylindrical coil. Therefore, approximately like in a beam path in a plane-parallel plate, the scattered light can be detected by the optional second optical imaging detector (D2) which is for instance arranged above the coil and faces the outer circumferential surface thereof.

Preferably, the detection is carried out continuously during rotation, i.e. during the winding or unwinding of the coil.

A material suitable for the ribbon is any brittle material which is sufficiently transparent to transmit light from one end face of the coil to the opposite end face, in particular by total reflection at the surfaces of the ribbon material transversely to the longitudinal extension thereof. Preferably, glass that is at least partially transparent is used as the ribbon material of the coil. The invention is also suitable for inspecting a laminated glass or a composite material including at least one glass layer.

The invention is particularly useful for inspecting ultra-thin glasses. In the sense of the invention, ultra-thin glasses refer to glasses having a glass thickness of not more than 200 µm. Other materials include rollable solar cell material or OLED (organic light emitting diode) material, and laminates comprising at least one glass layer, preferably an ultra-thin glass or an ultra-thin glass layer. A laminate including a glass layer refers to a laminate that comprises at least one layer of a further material in addition to the glass layer, or at least two glass layers laminated to one another.

Thus, the already wound ribbon areas of the coil are inspected repeatedly. Thereby, the phenomenon is taken into account that with increasing number of windings or turns of the coil, increasing surface loads may cause defects, such as cracks, in the coil. Consequently, it is possible to detect earlier and later damage such as for instance caused by tensile stresses in the region of the cut edge surfaces, by increasing local tensions around a defect such as bubbles or inclusions in the glass ribbon or (dirt) particles trapped between the ribbon layers, by inhomogeneous stress conditions during the winding of the ribbon exhibiting warpage or thickness variations, or in the edge region of an intermediate layer, etc.

In order to not only clearly differentiate or discriminate and detect the existence of a defect, but also its location in a certain area of the ribbon or in individual different layers of the ribbon, the longitudinal position of the defect can be deduced from the position of the defect in the image of the imaging detector and from the number of windings.

Preferably, intermediate layers are wrapped into the coil, which in particular serve to prevent the winding layers of the ribbon material, which would otherwise be directly superimposed, from scratching against each other, and to avoid strong adhesion of the winding layers to each other. The intermediate layers may be non-transparent or partially transparent, and/or the refractive index of the material of the intermediate layer is different from that of the coil material. These intermediate layers are advantageous for the invention, since they permit to more easily differentiate the individual different layers of the ribbon of the coil in the image of the imaging detector.

Therefore, according to one embodiment of the invention it is contemplated that intermediate layers preferably made of plastic material are wrapped into the coil, so that the imaging detector (D1) is able to discriminate and differentiate the individual layers of the ribbon of the coil. In case of a semi-transparent material or a material differing from the material of the coil in its refractive index, the optional second detector (D2) may optionally inspect a plurality of layers of the coil, and the location of a defect can be detected from the data of this detector.

Preferably, a plastic material is used for the intermediate layers. Another material such as a paper web could also be envisaged. The integrated or wrapped intermediate layers may therefore be used for counting the individual layers and thus for calculating the length of the coil and ribbon sections of the coil.

The method is also suitable for identifying a defect from a varying layer spacing between the ribbon surfaces, in particular by the first detector (D1).

The choice of the light source or light depends, among other things, on the material of the coil, i.e., for example, the materials of a laminate, possibly also on the material of the intermediate layers.

When space is limited, the light may as well be injected and captured using angle optics.

Preferably, a laser with anamorphic optics is used as a light source for line-shaped illumination of the coil. Alternatively, a linear LED array may be used. Telecentric lighting of the entire coil or of a portion thereof is likewise conceivable.

Optical imaging detector generally refers to a detector which performs localized measurements such that the measured values can be assembled into an image of at least a portion of the surface.

Detectors scanning the surface of the ribbon are not necessary here, since a ribbon wound into a coil is inspected simultaneously. Moreover, the method and device for inspecting and detecting defects, in particular cracks, do not require feeding means for advancing the ribbon relative to the assembly including the light source and the optical detector.

Generally, a defect, e.g. a crack, can be determined from the image data obtained by the optical imaging detector by evaluating the local brightness distribution.

In an advantageous embodiment of the method, at least one of the optical imaging detectors (D1 and/or D2) is a line scan camera, and an image is assembled from image lines sequentially captured by the line scan camera.

For area illumination or annular illumination of the coil, the coil is preferably illuminated using an axicon or an annular LED array, and a matrix camera is used at least as one of the optical detectors (D1 and/or D2). An axicon is a special conically ground lens imaging a point source to a line along the optical axis or transforming a light beam such as a laser beam into a ring or a beam having a ring-shaped beam cross section as seen in the beam direction.

To achieve (additional) depth discrimination of the defect, light-emitting diodes (LEDs) of different colors and/or with different timing may be used as a light source. Due to the different timing and/or color, the individual light sources and their beam paths in the coil can easily be distinguished by the detectors, in particular by the optional second imaging detector as well in this case.

When a multi-channel technology is employed, such as in particular described in DE 10 2011 113 670 A1, and when using different light sources staggered in the depth or in the radial direction of the coil, discrimination (for instance) of the z-position of the defect can be achieved by the second detector (D2). The depth can for instance be coded by light sources of different wavelengths, intensities, frequencies, and so on. Linear arrays of light-emitting diode comprising individually switchable, pulsable segments may likewise be used. Depth information is also coded in the color or signal waveform over time of the light scattered at a defect and exiting from the outer circumferential surface, and can be assigned on the basis of the signal of the second optical imaging detector (D2) facing the outer circumferential surface.

Preferably, at least two of the three means of the group comprising light source, imaging detector (D1), optional second imaging detector (D2), are arranged so as to be coplanar to each other, preferably all three components are coplanar to each other. That means, in the latter case the viewing directions of the detectors are in the same plane.

In a particular embodiment of the method, additional tilt angles can be set between the light source and the detectors, for switching between light-field and dark-field inspections.

Since the method of the invention is simply based on the rotation of the coil, it can be employed inline (i.e. during the manufacturing process) when the ribbon is wound, and offline for quality control and classification of the coil and for cutting to final dimensions for further processing. For example, a simple rotation of the coil in the measuring arrangement is sufficient for offline inspection in order to obtain an overview of the defect condition of the coiled ribbon. In particular, in the so-called "roll-to-sheet process" for delivered incoming articles, cut optimization can be performed based on the defect position determined during the unwinding operation, before the ribbon is separated into individual sheets.

Thus, the method and device of the invention may in particular be used in the production of rollable (ultra-thin) glass, rollable glass films, laminated rollable (ultra-thin) glasses and glass films, rollable solar cells and rollable organic light emitting diodes (OLEDs).

BRIEF DESCRIPTION OF THE DRAWINGS

The invention will now be described in more detail with reference to the accompanying drawings in which the same reference numerals refer to identical or similar elements and wherein.

DETAILED DESCRIPTION

Figure 1:
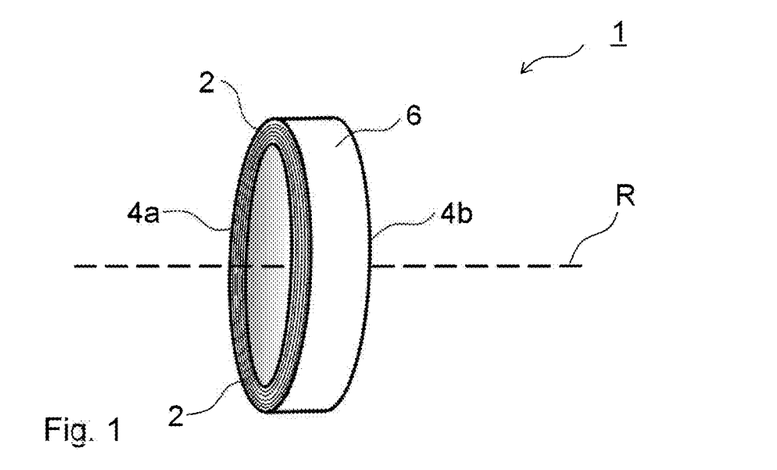
FIG. 1 is a perspective view which schematically illustrates a coil to be inspected.

FIG. 1 is a perspective view schematically illustrating a coil 1 with a rotation axis R. Coil 1 has the shape of a hollow cylinder in which the coiled edge surfaces 2 define the two end faces 4a, b.

Furthermore, coil 1 has two opposite ribbon surfaces 6, an upper ribbon surface 6a and a lower ribbon surface 6b, only a portion of the upper ribbon surface 6a being visible in FIG. 1, which portion defines the lateral or outer circumferential surface 6a of the hollow cylinder. The ribbon of coil 1 is made of brittle or fracture-prone material which is at least partially transparent, for example transparent glass, especially ultra-thin glass or laminated ultra-thin glass.

Figure 2:
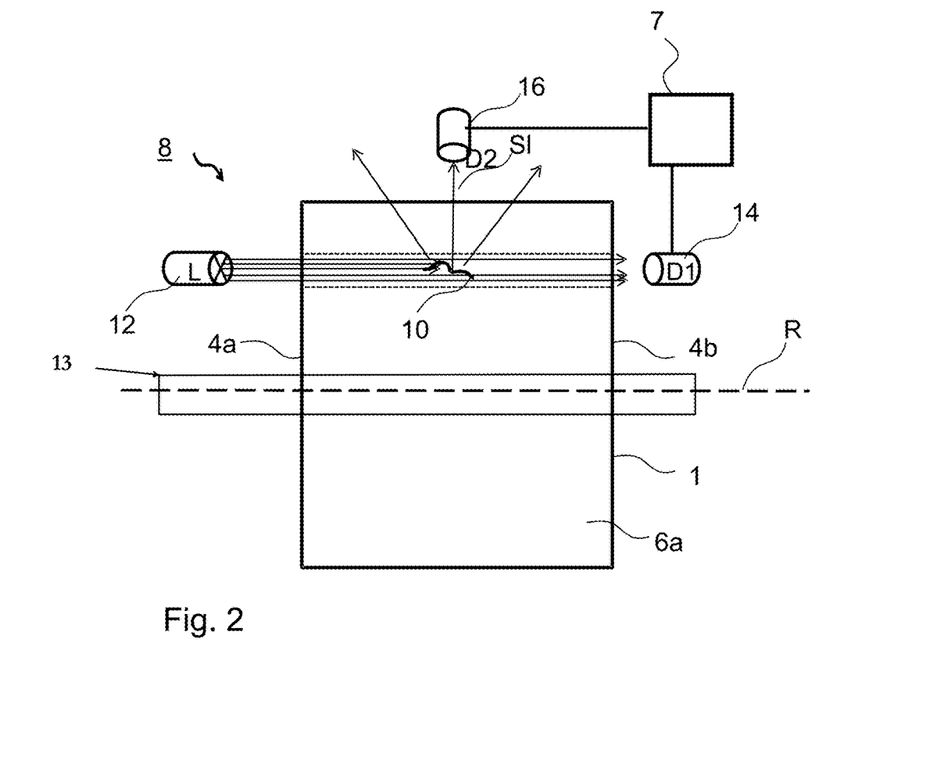
FIG. 2 schematically illustrates the configuration of a device for detecting defects according to the invention, showing a coil in a front plan view.

FIG. 2 schematically illustrates the configuration of a device 8 according to the invention for detecting defects, in particular a crack 10, showing a front view of the coil 1 to be inspected, with rotation axis R, in which a portion of the upper ribbon surface 6a which defines the outer circumferential surface 6a of the hollow cylinder, and the two end faces 4a and 4b of the coil 1 are visible.

Device 8 for detecting defects, in particular cracks 10, in ribbons of brittle or fracture-prone material which is at least partially transparent comprises a light source 12 (L) which is arranged with respect to a means for winding or unwinding the ribbon 13 in a manner so that the light is introduced into the end face 4a of the coil 1, while coil 1 rotates around rotational axis R and the ribbon continues to be wound or unwound. In the coil 1 the light is directed in the direction of the arrows from the light entrance side end face 4a to the light exit side end face 4b of the coil and exits at the light exit side end face 4b. Light source 12 is an annular LED array, or light-emitting diodes (LEDs) of different colors and/or with different timing.

When space is limited, the light may as well be injected and captured using angle optics.

Furthermore, as can be seen in FIG. 2, device 8 comprises an optical imaging detector 14 (D1), preferably a photodiode or a first camera which detects the light exiting from the end face 4b of the coil 1 in the direction of the arrows. In case of the absence of a defect or crack 10, the light will be guided in the at least partially transparent coil 1 by total reflection, and will be detected on the light exit side of the ribbon.

According to one embodiment of the invention, device 8 for detecting defects, in particular cracks 10, in the coil 1 further comprises, as shown in FIG. 2, a second optical imaging detector 16 (D2) which faces the outer circumferential surface 6a of the coil 1, preferably a second camera. In case of the presence of a defect in the ribbon, in particular a crack 10, this second detector 16 (D2) will detect the light deflected in coil 1 by being scattered at a defect or crack 10 so as to exit from the outer circumferential surface 6a in the direction of the arrows (scattered light Sl).

According to one embodiment of the invention, without being limited to the specific exemplary embodiment, the imaging detector D1 (14) is connected to an image processing means 7 of the device 8. This image processing means 7 may in particularly be adapted for detecting a defect 10 in the captured image and for outputting and/or recording an error signal upon detection of a defect. If a second imaging detector 16 is provided, it may also be connected to image processing means 7. Image processing means 7 may then be adapted for determining, on the basis of the image from the second detector 16, the position of a defect 10 in a direction transversely to the longitudinal extension of the ribbon material.

In case of homogenous lighting of an area or telecentric lighting of the entire coil 1 on the light entrance side thereof, a matrix camera can be used on the output side. In this case, inspection of the entire coil is possible without rotation thereof.

Preferably, at least two of the three means of a group comprising light source 12, detector 14 (D1), and second detector 16 (D2) are arranged so as to be coplanar to each other. Preferably, all three means mentioned are coplanar to each other. In such an arrangement, in particular if at least the two detectors are arranged so as to be coplanar to each other, any existing defects can be simultaneously detected by the two detectors.

Defects 10 or faults, i.e. non-planar surfaces with cracks, scratches, etc., interfere with the light path. At such anomalies, the light will be reflected or scattered towards the detector D2, e.g. a camera. These defects will appear bright in the camera image.

In case of lateral lighting on non-planar surfaces, the edge of a defect 10 facing the light will be bright and the edge of a defect 10 facing away from the light will be dark.

Generally, a defect, for example a crack 10, can be detected on the basis of the image data obtained from an optical imaging detector (D1 and/or D2) by an evaluation of the local brightness distribution.

The detector signals obtained are assembled into a surface image. The presence of a defect, e.g. a crack 10, can then be detected by a computing means, not shown in the figures, from the local brightness distribution in the surface image. If a defect or crack 10 was localized by the computing means, there are several possibilities of response to the existing defect. In the simplest case, the computing means can signal the presence of a defect. According to another embodiment of the invention, the obtained corresponding data are stored by the computing means, so that the location of a defect in the ribbon can again be located at a later time. However, it is also possible to perform automatic or semi-automatic control functions on the basis of the detected defects. For example, cutting may be optimized so that the individual sheets are separated from the ribbon in a manner so that the defect will not be present in any of the sheets.

Detectors scanning the surface of the ribbon are not required according to the invention, because a ribbon wound into a coil 1 is inspected simultaneously. Moreover, the method and device 8 for inspecting and detecting defects, in particular cracks 10, do not require feeding means for advancing the ribbon relative to the assembly of light source 12 and optical detector (D1 and/or D2), and that the detector signals are recorded by a computing device.

Moreover, the method may be adapted so that light sources (12) differently coded in color or time inject light into the light entrance side end face (4a) in the radial direction of the coil (1), and that on the basis of the light coded in color or time, which is scattered at a defect (10) and received by the second detector (D2, 16), an assignment of the depth of the defect (10) is made.

Figure 3:
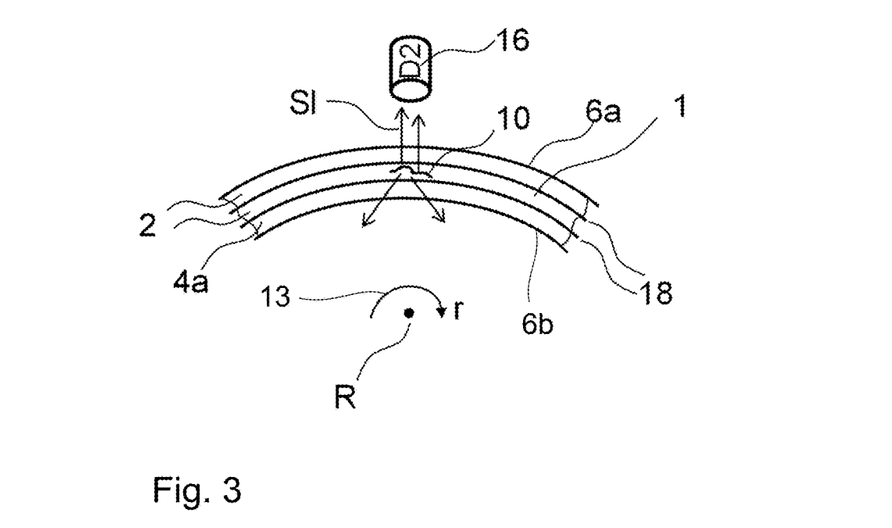
FIG. 3 is a side view of a portion of a coil, schematically illustrating a beam path in a (rotating) coil that includes a defect.

FIG. 3 shows a side view of a portion of coil 1 that includes a defect, in particular crack 10, the coil rotating about the rotation axis (R) in a rotation direction (r) by device 13, and schematically illustrates the beam path of the light Sl scattered at the defect or crack 10 out of the upper ribbon surface or outer circumferential surface 6a towards the second optical detector 16 (D2) arranged above the outer circumferential surface 6a of hollow cylindrical coil 1.

The portion of coil 1 with a defect or crack 10 shows the light entrance side end face 4a with edge surfaces 2 or layers of the coiled ribbon.

In order to not only clearly differentiate or discriminate and detect the existence of a defect 10, but also its location in a certain area of the ribbon or in individual different edge surfaces 2 or layers of the ribbon of coil 1, intermediate layers 18 are preferably wrapped into the coil 1, in particular plastic layers. The incorporated or wrapped intermediate layers 18 may thus serve to count the individual edge surfaces 2 or layers and thus for calculating the length of the coil and ribbon sections of the coil 1. For example, when intermediate layers 18 are used, the detector 16 (D2) in particular detects near-surface layers, and in case of a non-transparent intermediate layer the uppermost layer is detected.

Figure 4:
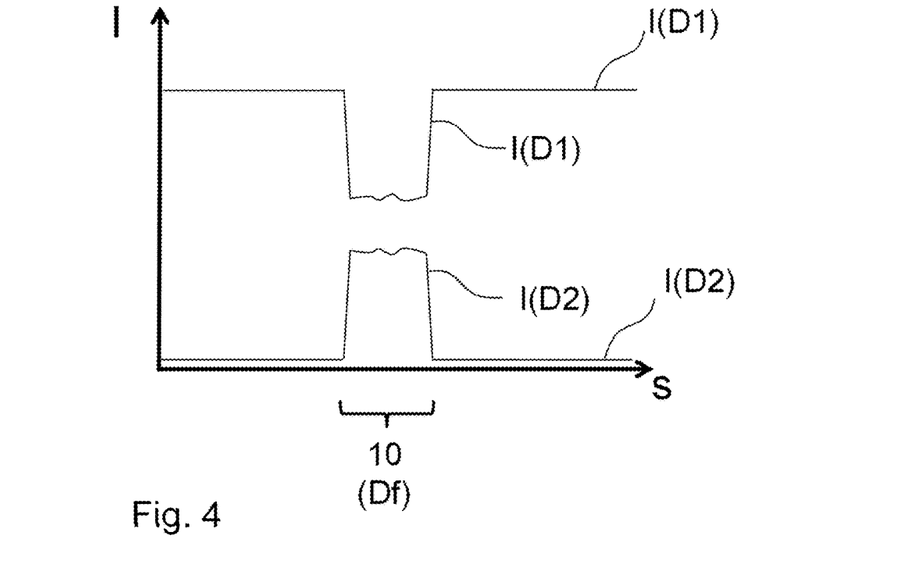
FIG. 4 is a graph of the intensity profiles of the light captured from a coil that includes a defect.

FIG. 4 shows a graph of intensity profiles I of the light beams as a function of the location S on the coil 1 having a defect or crack 10.

A defect or crack 10 in the ribbon thus leads to a deflection of the guided light out of the monitoring direction of imaging detector 14 (D1) and thus results in a local change in intensity of the light beams at detectors 14 (D1) and 16 (D2), namely usually a reduction in intensity I (D1) at imaging detector 14 (D1) and an increase in intensity I (D2) at the second detector 16 (D2) in the region of defect projection area 10 (Df).

Figure 5:
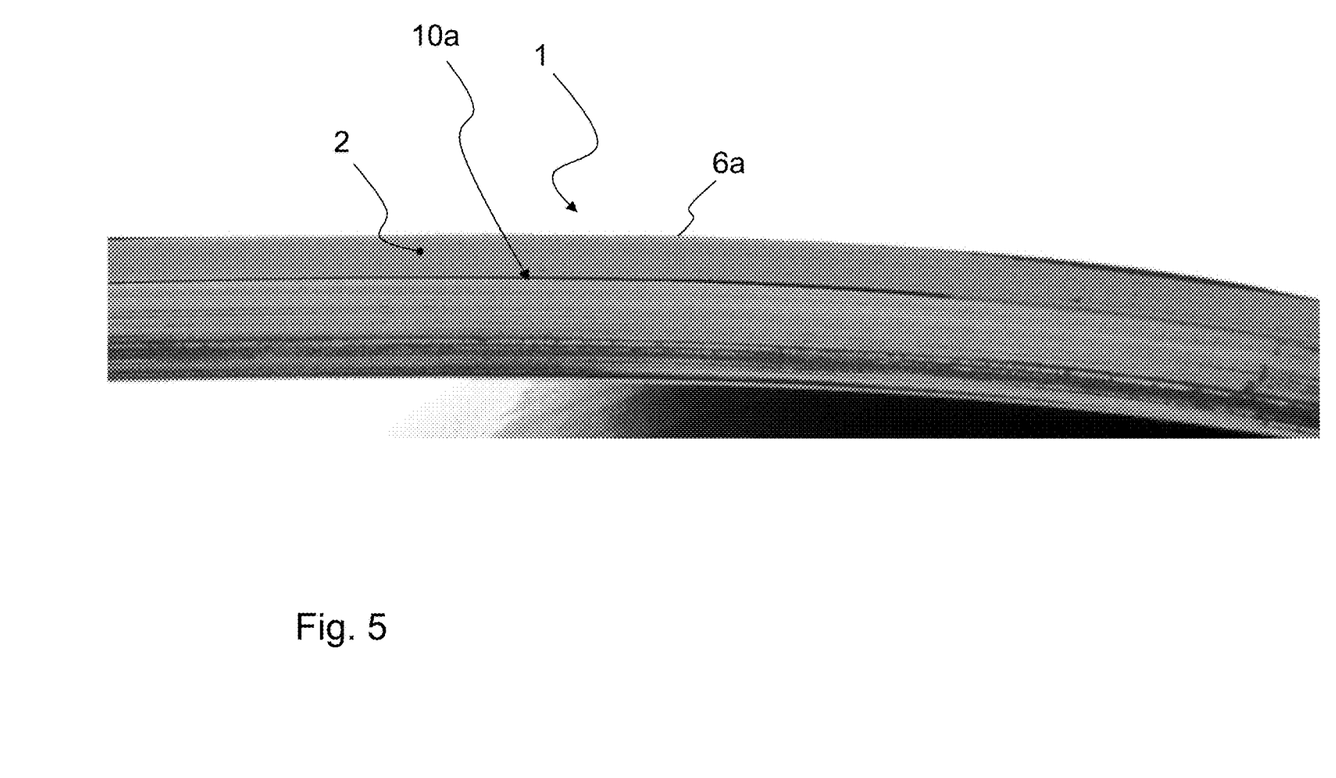
FIG. 5 is a photograph of a side view of a section of a rollable curved stack of ultra-thin glass with a longitudinal crack.

FIG. 5 shows a photograph of the light exit side end face of a coil 1 in the form of a coiled ultra-thin glass, captured by imaging detector 14. In the photograph, a defect 10 in the form of a longitudinal crack 10a is visible. In case of a longitudinal crack, the crack runs in parallel to the edge surfaces 2 of the glass ribbon. In the region of the longitudinal crack, the glass ribbon appears dark, since light transmission through the glass ribbon is intercepted there. As can be seen from the photograph, the crack and also the location thereof are readily detectable with the device according to the invention.

Figure 6:
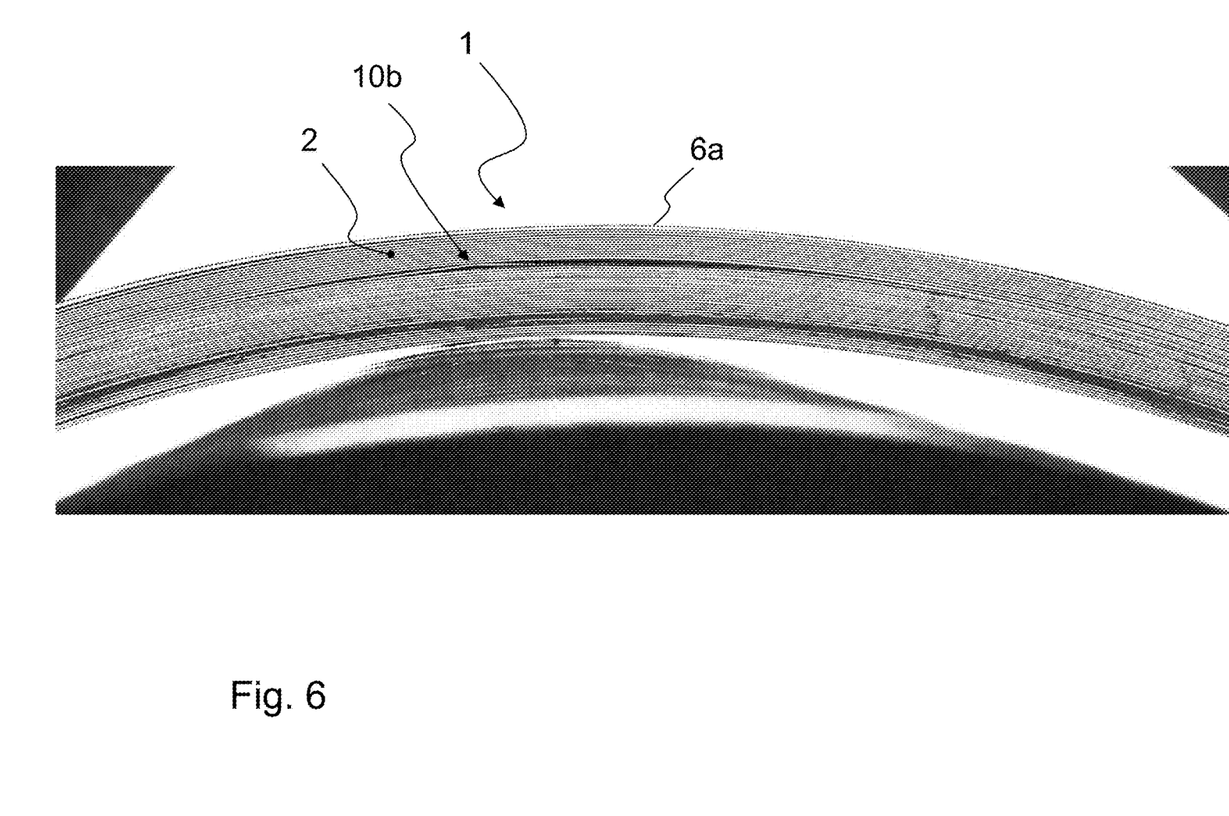
FIG. 6 is a photograph of a side view of a section of a rollable curved stack of ultra-thin glass with a transverse crack.

FIG. 6 also shows a photograph of the end face of a coil 1 in the form of a coiled ultra-thin glass as captured by imaging detector 14. This coil includes a defect 10 in form of a transverse crack 10b. In this case, the crack runs perpendicular to the edge surfaces 2 of the glass ribbon.

In case of a defect 10 which is not a purely transverse crack, the imaging detector 14 (D1) will detect a change in intensity, and the second detector 16 (D2) will detect light scattered out of the viewing direction perpendicularly to the upper surface 6a of the glass ribbon, in particular in case of near-surface glass layers and at least partially transparent intermediate layers.

If the coil 1 includes a purely transverse crack 10b, this crack will have no defect projection area (Df) in the viewing direction towards imaging detector 14 (D1), and therefore no change in intensity will be detected. However, a kink is visible in the corresponding glass layer at these points, that means there exists a local discontinuous change in curvature (FIG. 6).

It will be apparent to those skilled in the art that the invention is not limited to the embodiments described above, but may rather be modified in many ways without departing from the scope of the following claims. In particular, it is possible to combine the features of individual exemplary embodiments. Instead of a plastic film, another rollable material can be used as an intermediate layer, such as a paper web. Also, one or more further detectors may optionally be provided.

LIST OF REFERENCE NUMERALS

1 Coil
2 Edge surface
4a Light entrance side end face
4b Light exit side end face
6 Ribbon surfaces
6a Upper ribbon surface, outer circumferential surface of hollow cylinder
6b Lower ribbon surface
7 Image processing means
8 Device
10 Defect, in particular crack
10a Longitudinal crack
10b Transverse crack
12 Light source
14 Imaging detector (D1)
16 Second imaging detector (D2)
18 Intermediate layer, preferably of plastic material
R Rotation axis of coil 1
Rr Rotation direction of coil 1
Sl Scattered light
I Intensity of light beams
S Location on coil 1
Df Defect projection area

What is claimed is:

1. A method for detecting cracks in a ribbon of brittle or fracture-prone material that is at least partially transparent and wound into a coil, comprising the steps of:
   providing the ribbon in the coil with a shape of a hollow cylinder in which edge surfaces of the ribbon define two end faces and one ribbon surface defines an outer circumferential surface of the hollow cylinder;
   introducing light into a first of the two end faces so that the light is directed from a light entrance side at the first of the two end faces to a light exit side at a second of the two end faces and exits from the light exit side;
   detecting the light exiting from the light exit side with a first optical imaging detector so that, if a crack is present in the ribbon, the crack can be seen as a shading in an image captured by the first optical imaging detector caused by interruption of light transmission due to the crack.

2. The method as claimed in claim 1, where the step of detecting with the first optical imaging detector further comprises detecting while the coil is wound or unwound.

3. The method as claimed in claim 1, wherein the step of providing the ribbon in the coil comprises providing, as the ribbon, at least one material selected from the group consisting of glass, ultra-thin glass, rollable solar cell material, rollable OLED material, a laminate comprising at least one glass layer, and a laminate comprising at least one ultra-thin glass layer.

4. The method as claimed in claim 1, wherein the step of introducing the light comprises activating a light source selected from the group consisting of a line-shaped lighting device, a laser with anamorphic optics, a linear LED array, and a telecentric lighting device, an LED array having LED's of different colors, and an LED array having LED's with different timing.

5. The method as claimed in claim 1, further comprising identifying a defect based on a varying layer spacing between the outer circumferential surfaces.

6. The method as claimed in claim 1, wherein the step of providing the ribbon in the coil comprises wrapping an intermediate layer with the ribbon into the coil so that the first imaging detector discriminates and differentiates individual layers of the ribbon in the coil.

7. The method as claimed in claim 6, wherein the intermediate layer comprises a plastic material.

8. The method as claimed in claim 1, further comprising detecting the light exiting from the outer circumferential surface with a second optical imaging detector so that, if a crack is present in the ribbon, the light in the coil is scattered at the crack and exits from the outer circumferential surface, which is detected by the second optical imaging detector.

9. The method as claimed in claim 8, wherein the step of detecting with the second optical imaging detector further comprises detecting while the coil is wound or unwound.

10. The method as claimed in claim 8, wherein at least one of the first and second optical image detectors comprises a line scan camera, the method further comprising assembling an image from image lines sequentially captured by the line scan camera.

11. The method as claimed in claim 8, wherein at least one of the first and second optical image detectors comprises a matrix camera, and wherein the step of introducing the light comprises using an axicon or an annular LED array for area illumination or annular illumination.

12. The method as claimed in claim 8, wherein the step of introducing the light comprises activating light sources that are coded by different colors or different timing, the method further comprising assigning a depth to the crack based on the light coded by the different colors or the different timing and received by the second optical image detector.

* * * * *